US011389238B2

(12) United States Patent
Franceschina et al.

(10) Patent No.: US 11,389,238 B2
(45) Date of Patent: Jul. 19, 2022

(54) DEVICE FOR DERMATOLOGICAL TREATMENT

(71) Applicant: QUANTA SYSTEM S.P.A., Milan (IT)

(72) Inventors: Cesare Plinio Franceschina, Valdidentro (IT); Marco Tagliaferri, Florence (IT); Fabio Cannone, Melzo (IT)

(73) Assignee: QUANTA SYSTEM S.P.A., Milan (IT)

( * ) Notice: Subject to any disclaimer, the term of this patent is extended or adjusted under 35 U.S.C. 154(b) by 0 days.

(21) Appl. No.: 17/283,170

(22) PCT Filed: Oct. 4, 2019

(86) PCT No.: PCT/IB2019/058454
§ 371 (c)(1),
(2) Date: Apr. 6, 2021

(87) PCT Pub. No.: WO2020/075025
PCT Pub. Date: Apr. 16, 2020

(65) Prior Publication Data
US 2021/0307827 A1    Oct. 7, 2021

(30) Foreign Application Priority Data

Oct. 8, 2018   (IT) .......................... 102018000009253

(51) Int. Cl.
*A61B 18/20*      (2006.01)
*A61N 5/06*       (2006.01)
(Continued)

(52) U.S. Cl.
CPC .......... *A61B 18/203* (2013.01); *A61N 5/0616* (2013.01); *A61B 2018/00023* (2013.01);
(Continued)

(58) Field of Classification Search
CPC ........ A61B 18/203; A61B 2018/00803; A61B 2018/00797; A61B 2018/00023;
(Continued)

(56) References Cited

U.S. PATENT DOCUMENTS 6,514,278 B1 *   2/2003   Hibst ................... A61B 18/203
                                                            606/11
6,575,969 B1 *   6/2003   Rittman, III ....... A61B 18/1482
                                                            606/41
(Continued)

*Primary Examiner* — Gary Jackson
*Assistant Examiner* — Sebastian X Lukjan
(74) *Attorney, Agent, or Firm* — Dickinson Wright PLLC; Andrew D. Dorisio (57) ABSTRACT

A system for the treatment of targets under the skin of a patient comprising: a laser device for emitting a first series of laser pulses towards an area of the skin of a patient, where a target which must be reached by said laser pulses is located under said skin; a cooling system of said area of the skin by means of a cooling fluid; a first measurement sensor of a first temperature of said area of skin; a second measurement sensor of the temperature of said cooling fluid; said computer which receives the signals from said first and second temperature measurement sensor; said computer controls said laser device that emits a first series of laser pulses having predetermined power, duration and spacing; said temperature measurement sensor measures the temperature of said area of skin, following said first series of laser pulses; said computer calculates the predicted temperature reached of said area of the skin following the emission of a second series of pulses having said predetermined power, duration and spacing.

8 Claims, 8 Drawing Sheets

(51) Int. Cl.
*A61N 5/067* (2006.01)
*A61B 18/00* (2006.01)
(52) U.S. Cl.
CPC ............... *A61B 2018/0047* (2013.01); *A61B 2018/00797* (2013.01); *A61B 2018/00803* (2013.01); *A61N 5/067* (2021.08)
(58) Field of Classification Search
CPC .. A61B 2018/0047; A61B 2017/00172; A61B 2018/00452; A61B 2018/00642; A61B 2018/00011; A61B 2018/00702; A61B 2018/2253; A61N 5/0616; A61N 2005/067; A61N 5/0625; A61N 2005/0626
See application file for complete search history.

(56) References Cited

U.S. PATENT DOCUMENTS

| | | | |
|---|---|---|---|
| 2005/0045189 A1* | 3/2005 | Jay | A61B 5/1034 128/898 |
| 2009/0012515 A1 | 1/2009 | Hoenig et al. | |
| 2009/0125018 A1* | 5/2009 | Merrick | A61B 18/12 606/41 |
| 2014/0025033 A1 | 1/2014 | Mirkov et al. | |
| 2014/0121631 A1 | 5/2014 | Bean et al. | |
| 2015/0231418 A1* | 8/2015 | Kim | A61N 7/02 601/3 |
| 2018/0140866 A1* | 5/2018 | Daly | A61B 18/203 |

* cited by examiner

DEVICE FOR DERMATOLOGICAL TREATMENT

The present invention relates to a system for dermatological treatment and in particular a system for the treatment of targets within the skin and even more in particular to a system for determining the correct dosimetry for photo-induced heat treatment targeted at specific chromophores incorporated in a medium or more in general in a multi-layer structure, and to the related method.

The use of electromagnetic radiation for dermatological treatments, including, for example, hair removal, treating acne, broken blood vessels, unwanted tattoos, chromophores and more in general targets incorporated in a medium such as the skin, is currently a widespread technique which, however, has many aspects that make its use critical. The core of these techniques is to provide the "correct" dose of electromagnetic radiation to send sufficient thermal energy to damage the target, without damaging the surrounding tissue and the layers of skin above, hence permanently damaging the tissue and causing the patient pain during and after the treatment.

It is known that during different types of dermatological treatments, such as those indicated above, the user/dermatologist does not have access to a system that allows the temperature of the target positioned under the surface of the skin to be known, and the correct dose of electromagnetic radiation to damage the target to be determined, in conditions that are safe for the patient and effective for the treatment.

The critical aspects related to this approach are due to the variation of the parameters of the biological tissue that surrounds the target, to the variation of the physical parameters of the target to be treated and to variability of the psycho-physical conditions of the patient.

Moreover, the variation within the system, used for the dermatological treatment, should also be considered.

Evaluation of all these variations during dermatological treatment with electromagnetic radiation appears extremely complex and is currently managed by the experience of the user/dermatologist.

It is evident for the expert that a correct and/or complete control of the aforesaid variables can facilitate a correct analysis and hence a better prediction of the results, as well as of the potential risks for the patient, including burning of the skin, scars, damage to the surface tissue, internal damage to the skin, etc., in some cases produced without reaching the desired objective.

An example of variability, known to the person skilled in the art, is the different thermal response of the different parts of the skin of the human body. A same area of the human body can sometimes have significant differences in the temperature of the skin from one part to the next, with a hotter region and other colder regions. Moreover, in some cases the heat transfer speed is greater than in others. This can be due to the presence of osseous tissue or to a higher or lower blood perfusion speed and finally to the psycho-physiological conditions of the patient. Added to this are further inherent distinctive elements: age, gender and race.

To obtain the desired result, the user/dermatologist relies on his/her experience, directly observing the thermal response of the surface of the skin.

It is clear to the person skilled in the art that the availability of a system that enables the variables of the parameters in the dermatological treatment to be controlled represents an innovative and inventive aspect in the field of dermatology.

Some systems have integrated a skin surface temperature sensor, or subcutaneous temperature sensors have been inserted into the skin of the patient, or molecular dyes that vary their luminescence on the basis of the temperature reached have been added. The first approach gives a safe indication of the surface temperature of the skin but does not allow any information on the temperature of the target positioned below the surface of the skin to be obtained. The other two approaches are decidedly more invasive for the patient.

Moreover, the introduction of a sensor to measure the skin surface temperature is only useful to prevent surface damage to the skin during treatment; with this system it is not possible to know and predict the evolution of the thermal gradient in the space, i.e., in various portions of the skin (target and not), and in time, i.e. during and at the end of the process and, even more importantly, the temperature value that will destroy the target.

To increase the probability of success (thermal damage to the target), avoiding damage to the surrounding tissue, current methods and systems are based on different treatment steps: pre-cooling, pre-conditioning of the radiation (i.e., pre-heating) and radiant heat (i.e., treatment), which however have various limits.

As the only non-invasive method of delivering laser radiation to subcutaneous target areas, for example in the dermis (the underlying skin), is to transmit the radiation to this area through the overlying cutaneous area of the epidermis, a part of the incident radiation is in any case absorbed by the overlying area of the skin and this can cause irreversible damage to the tissue, such as scars, and cause the patient pain.

It is also known that the amount of energy that must be used in the treatment increases in relation to the depth of the target. This implies the use of a more powerful laser system and emissions of a longer duration. This further increases the possibility of damaging the overlying skin and the non-target tissues.

Consequently, in order to protect the non-target tissues from the effect described above, many procedures require the epidermis to be efficiently cooled (pre-cooling).

This pre-cooling step is then followed by a pre-heating step and by an actual treatment step.

In some cases, the pre-heating protocol and the treatment protocol are performed by the same laser, although the two protocols involve different laser settings and application parameters, thus causing further complexity in the determination of the correct treatment dosimetry and in the construction of the treatment apparatuses.

The cooling process can lead to negative results. Appropriate use of cooling, with the understanding of how much heat must be released, of how much cooling is required and at what temperature the contact surface should be maintained are key points for efficacious treatment without side effects. (Willey et al. Complications of Laser Dermatologic Surgery, Lasers in Surgery and Medicine 38: 1-15 (2006)).

The laser system for the treatment of the sebaceous gland has been described in the past, for example by the documents WO2017077427 and WO2017109667.

The object of the present invention is a method and/or system capable of reaching the thermal damage temperature of a biological target located within the skin, based exclusively on reading the temperature on the cutaneous surface, avoiding damage to and undesirable effects on the surrounding and underlying tissue.

According to the present invention, these objects and others yet are achieved by a system and by a method described in the appended claims.

A characteristic of the present invention is to provide the temperature value of each portion of the skin, (chromophore, particles, layers of the skin, surface of the skin, blood vessel, sebaceous gland, hairs, pigmented freckles) during the dermatological treatment. In this way, it is possible to know whether the damage temperature of the target has been reached.

A further characteristic of the present invention is to introduce a predictive system, in real-time, to provide the correct dose of electromagnetic radiation required to guarantee damage of the target, avoiding biological damage such as burns, or other temporary and/or permanent damage of the skin, thereby diminishing any form of pain for the patient.

A further characteristic of the present invention is to provide a predictive system in real-time for reaching the damage temperature of the target, preventing biological damage such as burns, or other temporary and/or permanent damage of the skin, thereby diminishing any form of pain for the patient.

A characteristic of the present invention is to interrupt the treatment in the event in which the skin of the patient shows a sudden abnormality, or the patient feels sudden discomfort. In some cases, the patient's discomfort becomes obvious with an increase in blood pressure and consequently of the temperature of the surface of the skin. As the present invention predicts this temperature increase in real-time, in extreme cases emission and treatment in general are interrupted.

Another characteristic of the present invention is that of monitoring in real-time the cooling process (pre-cooling, cooling during laser treatment and post-cooling) avoiding internal or external damage to the skin due to an excess of cold or an excess of heat. In fact, the uniformity value of the surface temperature and the temperature value before the start of a laser pulse are monitored in real-time.

Another characteristic of the present invention is that of performing a pre-treatment session in which the operator develops a personalised treatment protocol based on definition of the treatment parameters for the different areas of the skin within the complete area to be treated.

The characteristics and advantages of the present invention will be apparent from the following detailed description of a practical embodiment thereof, illustrated by way of non-limiting example in the accompanying drawings, wherein.

Figure 1:
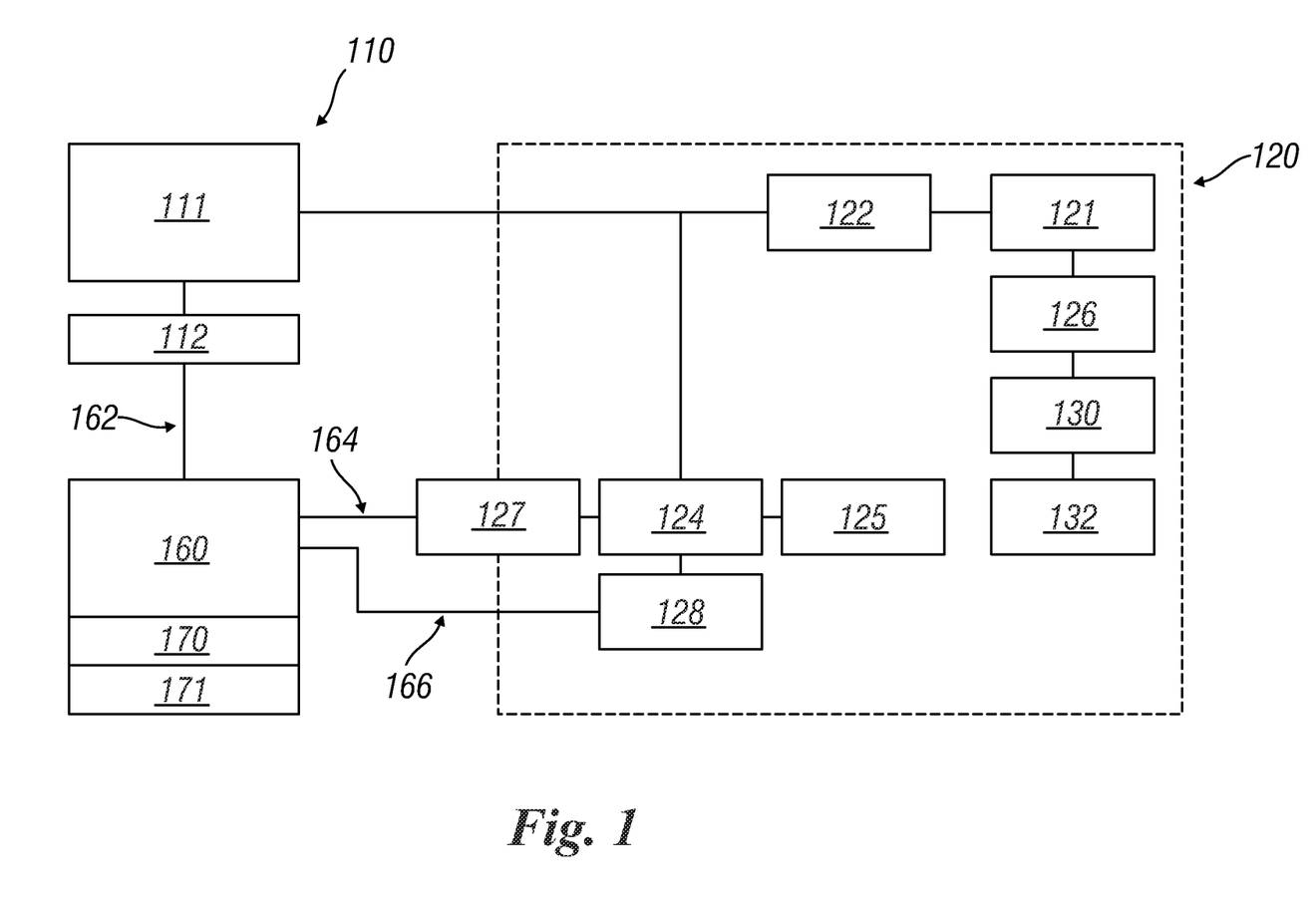
FIG. 1 illustrates a block diagram of an example of photothermal treatment system, according to an embodiment.

With reference to the accompanying figures, FIG. 1 shows an example of a targeted photothermal treatment system for targeting specific chromophores incorporated in a medium such as the skin and heating the target to a sufficiently high temperature to damage the target without damaging the surrounding medium. The system can be used, for example, for targeted photothermal ablation of the sebaceous glands, saving the epidermis and the dermis that surround the target sebaceous glands.

Again, with reference to FIG. 1, a photothermal treatment system comprises a cooling unit 110 and a laser treatment unit 120. The cooling unit 110 can apply the cooling fluid before the treatment (pre-cooling), during the treatment and after the treatment (post-cooling). The cooling unit 110 provides a cooling mechanism, for example through contact or by means of direct cooling of the air, in the treatment area, i.e., the area of the outer layer of the skin overlying the target. The cooling unit 110 communicates with a control device 122 in the treatment unit 120. It should be noted that, while the control device 122 is shown contained inside the treatment unit 120, the control device 122 could also be positioned in the cooling unit 110.

The controller 122 also controls other components inside the treatment unit 120, such as a laser 124, a display 126, a skin temperature sensor 128, a pedal switch 130, and an emergency on/off switch 132.

The laser 124 supplies the laser energy for the treatment protocol and the controller 122 adjusts the specific settings for the laser, such as the output power and the pulse time. The laser 124 can be a single laser or a combination of two or more lasers. If more than one laser system is used, the laser outputs are optically combined to function as a more powerful single laser, for example as described in the documents WO2017109667 and WO2017077427. The display 126 can show information such as the operating conditions of the cooling unit 110, of the laser 124 and of the other statuses of the system. Through the display 126 it is possible to manage the laser system 124, the cooling unit 110 and the scanner 160. The temperature sensor 128 is used to monitor the temperature of the surface of the skin in the treatment area that is used by the controller 122 to adjust the treatment protocol. The device 128 is an infrared thermal sensor. The controller 122 also interfaces with the pedal switch 130 to remotely switch on or off the laser 124 and/or the cooling unit 110. It is also possible to add further photodiodes 125 or other sensors to monitor the energy level of the energy emitted by the laser 124. A mechanical or electronic shutter 127 is positioned before the delivery optical fibre 164 to interrupt the laser radiation if necessary. A computer 121 is connected to the controller 122 and can evaluate in real-time all the process parameters coming from the skin temperature sensor 128 and from the photodiode 125, to activate the control cooling unit 111, the laser 124 and the scanner 160.

Continuing to refer to FIG. 1, the treatment system includes the cooling unit 110. A control board 111 allows the cooling unit 110 to communicate with the treatment system 120. Moreover, the cooling unit 110 is provided with sensors 112 of the cooling fluid such as: air temperature sensors, pressure sensors, such as hot wire anemometers to monitor all the physical parameters of the air flow incident on the skin 171 through the surface of the skin 170. In the event of cooling of the surface of the skin 170 being performed with techniques different from an air flow, all the sensors must be implemented to measure the physical quantities involved in cooling the surface of the skin.

In the embodiment illustrated in FIG. 1, the treatment unit 120 supplies laser energy with a single setting that is used both for pre-conditioning of the treatment area, and for treatment of the target. That is, rather than sequentially supplying laser energy optimised for pre-conditioning followed by a different laser energy optimised for the treatment, the treatment unit 120 supplies the same laser energy used both for pre-conditioning and for the treatment in a single and continuous application protocol without modifying the laser energy settings. This integrated protocol allows time to be saved and simplifies application of the treatment.

Figure 2:
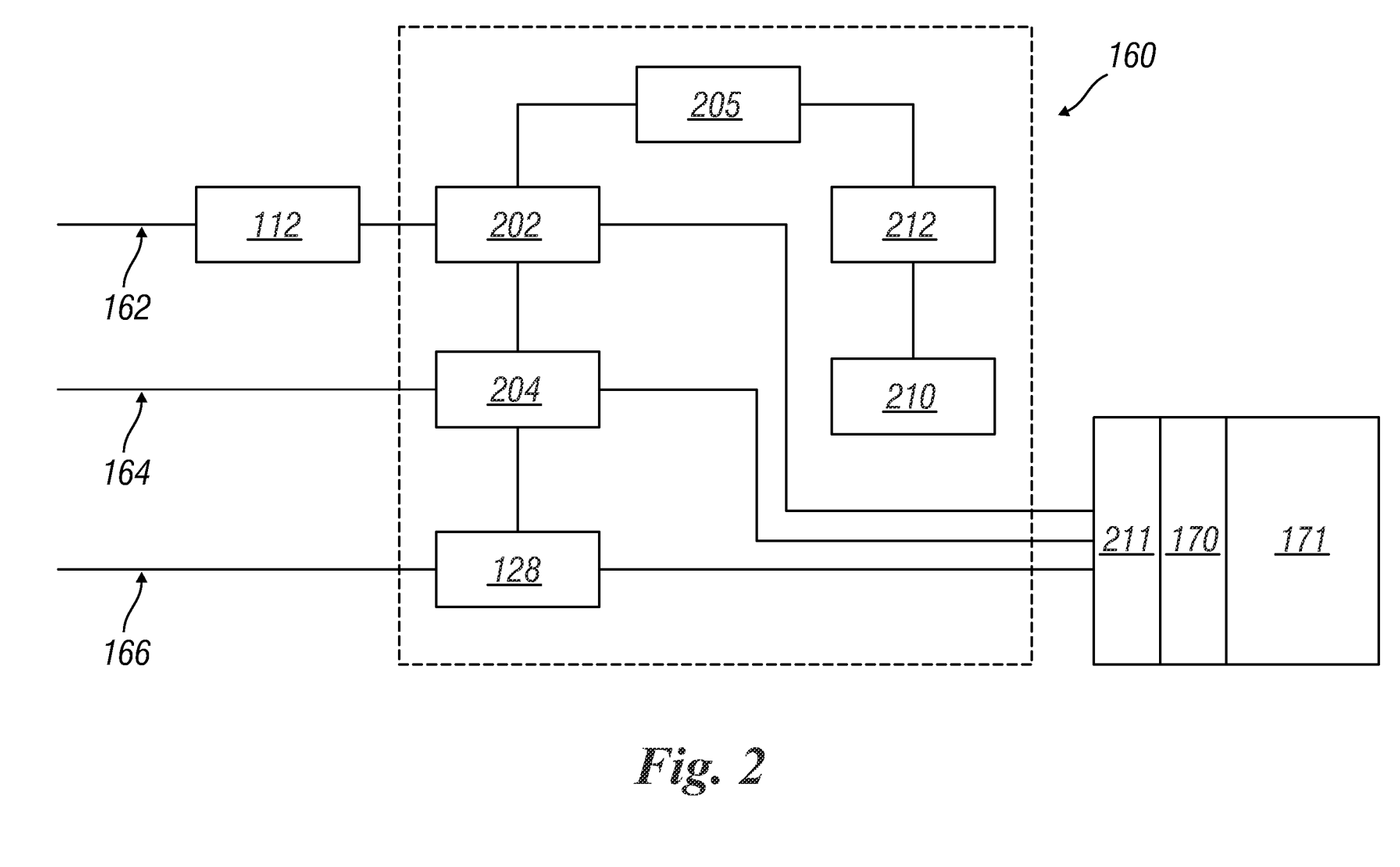
FIG. 2 illustrates a block diagram of an example of a scanner arrangement for use with the photothermal treatment system, according to an embodiment.

With reference to FIG. 2, the treatment system 120 further comprises a scanner 160, which is the portion of the device (handpiece) held by the user. The scanner 160, which is in contact with the skin 171 through the surface 170 of the skin, can be produced, for example, with a shape similar to a gun to facilitate handling by the user. The scanner 160 communicates with the cooling unit 110 through a tube 162, so that the cooling protocol can be applied using the scanner 160. The scanner 160 is connected to the temperature sensor 128, through a connection 166, and to the sensor 112 of the cooling fluid, to send the data to the controller 122. Moreover, the scanner 160 includes an on/off switch 210 for switching the laser 124 on/off and, optionally, comprises a monitor 212 of the scanner 160, which indicates the operating status of the scanner 160, for example whether the laser is used. A control board 205 allows the scanner unit 160 to communicate with the treatment system 120. The output from the laser system 124 is connected with the scanner 160 through the optical fibre 164, so that the treatment protocol can be applied using the scanner 160. The fibre 164 can, for example, be a fibre three metres in length with a square cross-section.

The cooling connection 162 is connected to a cooling delivery unit 202, which is configured to deliver the cooling fluid (for example a current of cold air) to the treatment area. The cooling delivery unit 202 is connected with a tip 211, which is in contact with the surface of the skin 170. The tip 211 is designed so as to ensure uniform distribution of the temperature on the surface of the skin during cooling or at most a point-to-point variation of +/−2° C.

Figure 3:
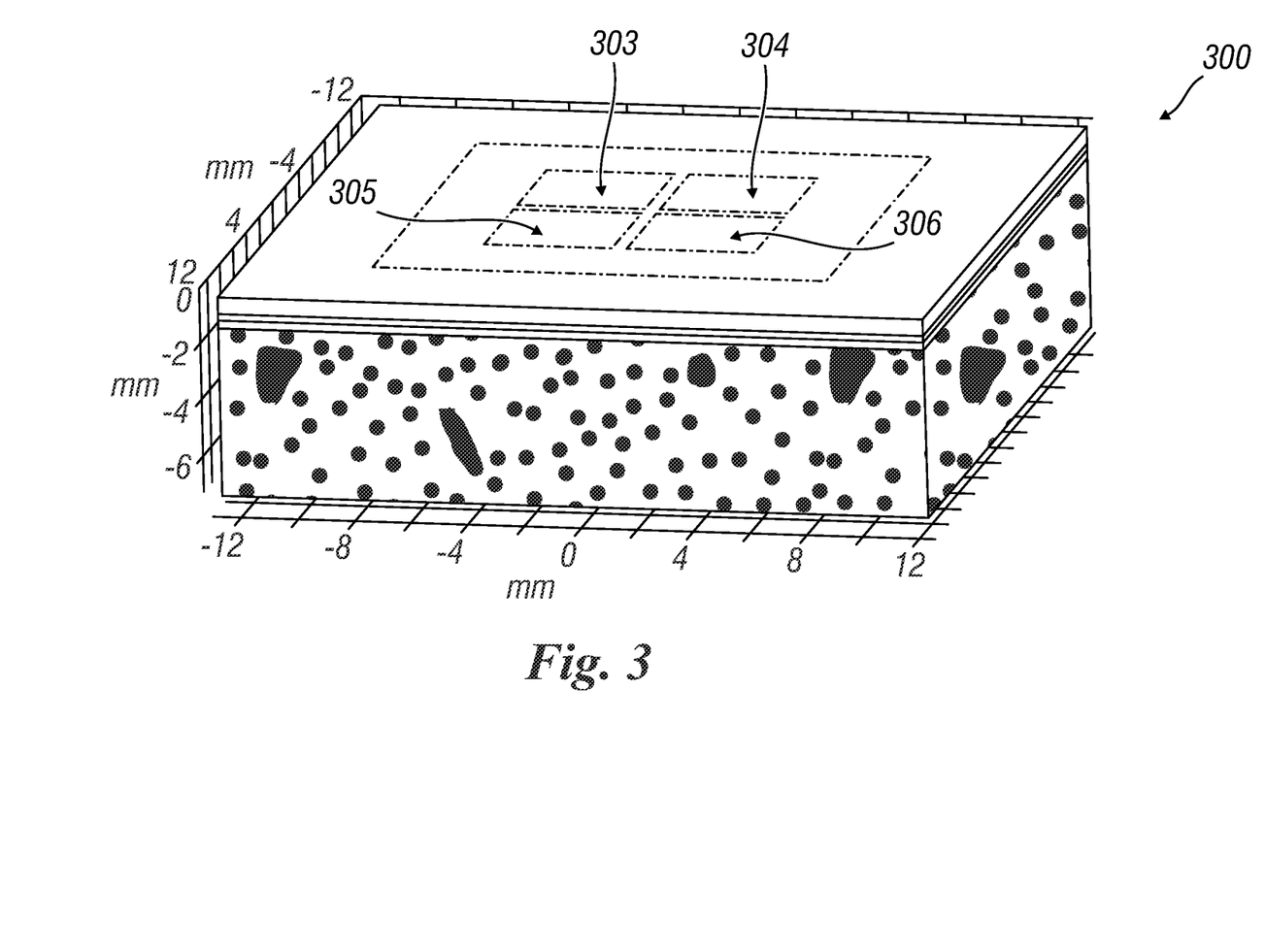
FIG. 3 illustrates an example of a treatment matrix arrangement, according to an embodiment.

FIG. 3 shows an example of treatment area that covers the chromophores to be treated. A virtual grid configuration is superimposed over the treatment area. An example of grid configuration 300 includes the four blocks 303, 304, 305 and 306, arranged in a 2×2 matrix. Many other grid configurations are possible, such as 1×1, 2×1, 2×2, 3×2, 2×3, 3×4, 3×3, etc. The beam could also be spaced or superimposed between the blocks.

The pre-cooling protocol can include, for example, the application of a current of cold air through the treatment area for a prescribed time, for example 10 seconds. After pre-cooling, the cooling mechanism can remain active and start the treatment protocol. In an embodiment, laser beams with a square section are used in combination with a scanner apparatus to sequentially apply the laser pulse to the blocks 303, 304, 305 and 306. According to an embodiment, the pre-conditioning/photo-treatment protocol includes the application of a predetermined number of light pulses on each of the blocks in the treatment area, with the blocks that are treated sequentially. In another embodiment, the blocks are treated in a random order.

Figure 4:
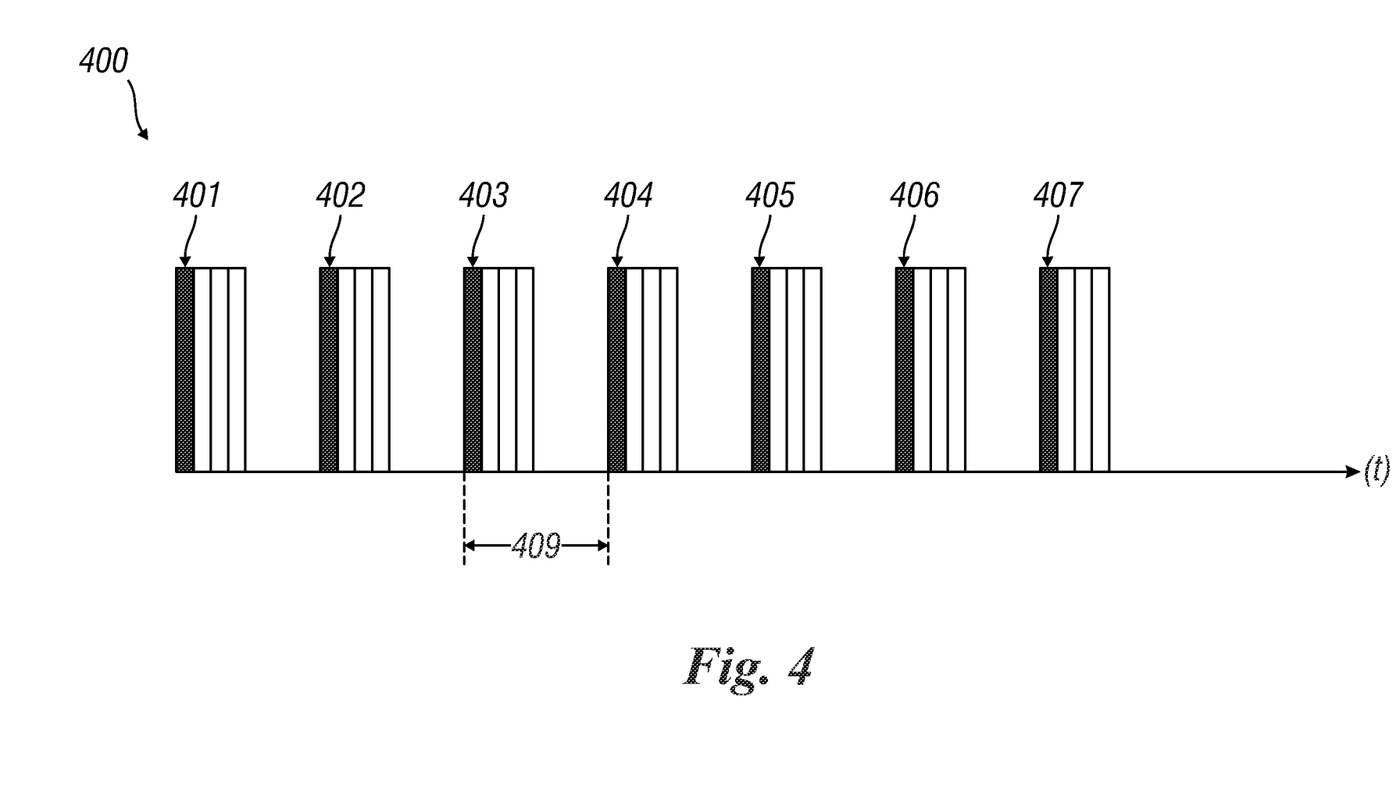
FIG. 4 shows an example of a diagram of a set of light pulses suitable for use as integrated treatment protocol, according to an embodiment.

FIG. 4 illustrates an example of a set of pulses suitable for the pre-conditioning/photo-treatment protocol according to an embodiment. A sequence 400 includes light pulses 401, 402, 403, 404, 405, 406 and 407 which are applied to one of the blocks 303-306 inside the treatment area. In an embodiment, all seven of the laser pulses are of the same power and are separated by a uniform pulse separation time 409 called matrix pulse delay. In an example, the duration of the laser pulse 401 is of 150 milliseconds and separation between the groups of pulses is of 2 seconds. The purpose of the separation between the sequence of pulses, for example of 2 seconds, is to allow the overlying skin and the underlying skin in the block to cool to prevent damage. During the separation time of the pulses, the laser can be sent to the other blocks in the treatment area to increase the efficiency of use of the laser.

Figure 5:
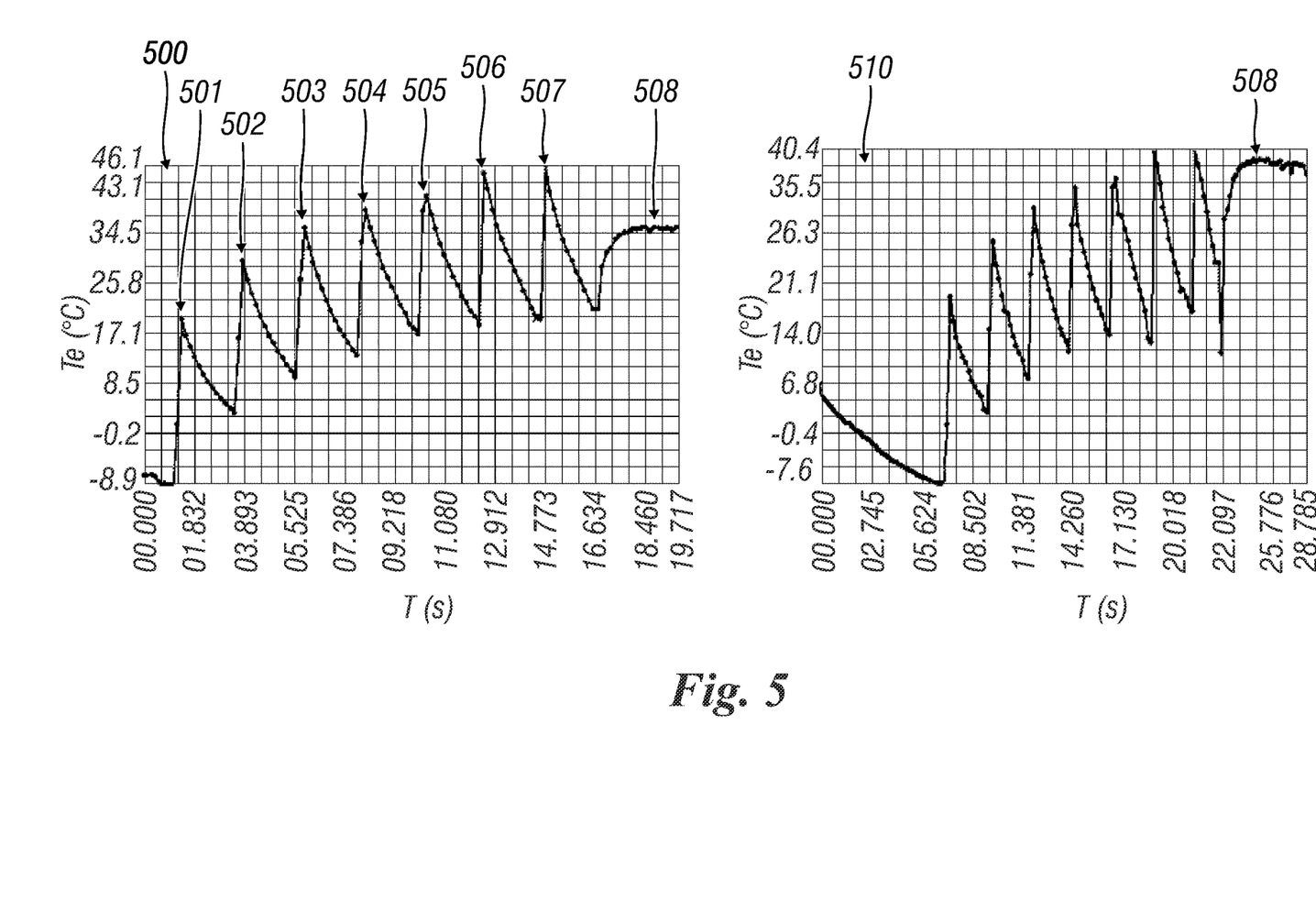
FIG. 5 shows the graph of the temperatures measured on the surface of the skin as a function of time as the pulses of the treatment are applied, on the left a portion of skin of the face and on the right a portion of skin of the neck, according to an embodiment.

FIG. 5 illustrates the example of surface temperature of the skin of a set of pulses suitable for the pre-conditioning/photo-treatment protocol as illustrated in FIG. 4, according to an embodiment. The sequence 500 or 510 includes the peak temperatures 501, 502, 503, 504, 505, 506, 507 recorded with the skin temperature sensor 128 on one of the blocks of skin, for example 303, respectively due to the light pulses 401-407.

FIG. 5 shows the post-cooling step 508, which follows the pre-conditioning/photo-treatment protocol. In this step, the cooling unit 110 continues to function for a time such as to return the temperature of the surface of the skin to a correct physiological temperature (for example 37° C.). The post-cooling time is adjusted and controlled by the computer 121 that, analysing the temperature value read by the skin temperature sensor 128 and the physical parameters of the cooling fluid, read by the cooling sensor 112, by means of the controller 122 controls operation of the regulator of the cooling unit 111.

Figure 6:
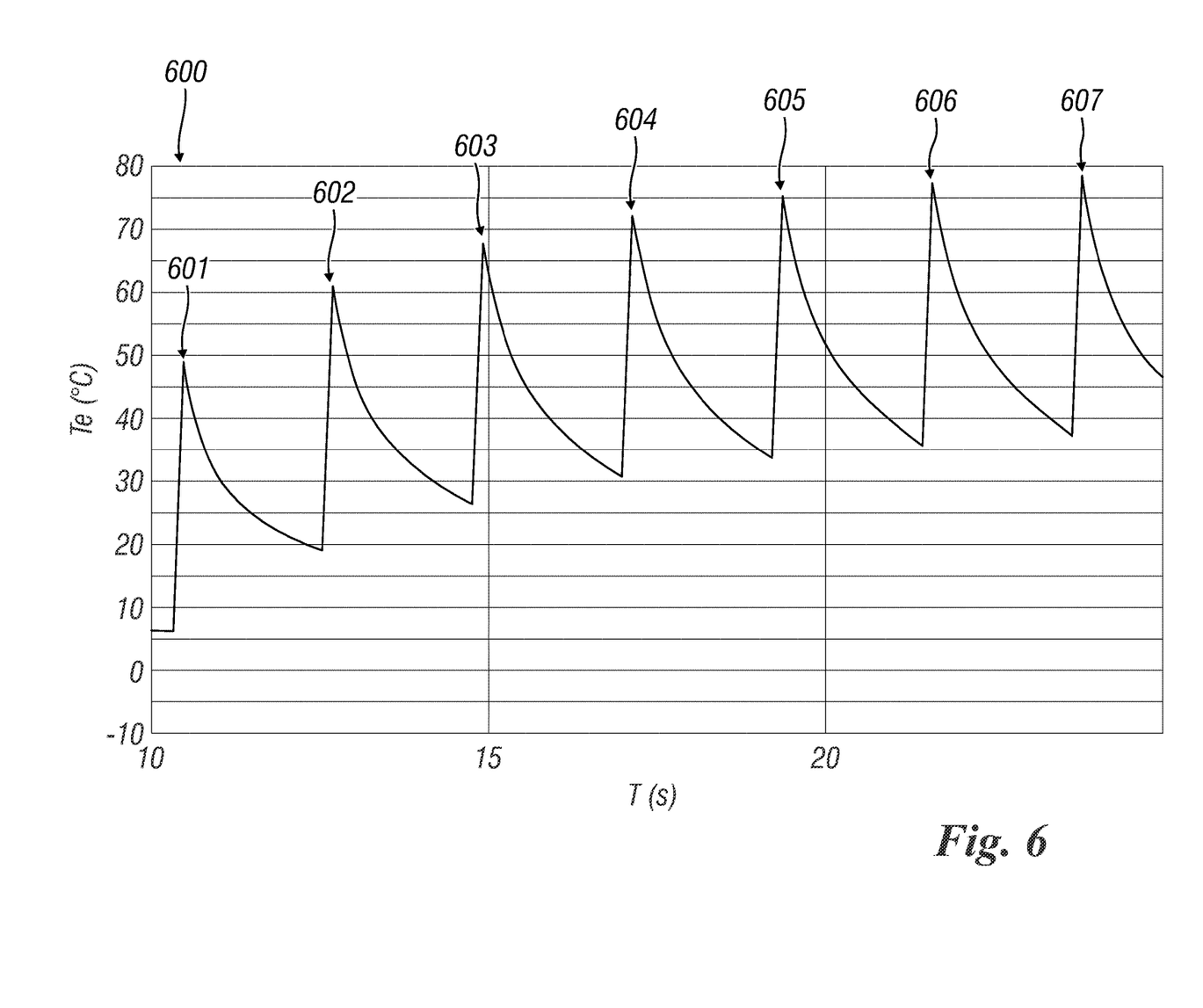
FIG. 6 shows the estimated temperature at the sebaceous gland target as a function of time when the pulses of the treatment are applied thereto, according to an embodiment.

FIG. 6 shows the temperature calculated on the target chromophore, in this example at 800 microns from the surface of the skin with laser pulses such as those shown in FIG. 4.

Therefore, the pulse 400 of the sequence of laser pulses induces a sequence of peak temperatures on the surface of the skin 500 that induces a peak temperature sequence 600 inside the skin composed of seven peak temperatures 601, 602, 603, 604, 605, 606 and 607. A clear correlation can be noted between the light pulses 401-407, the surface temperature peaks of the skin 501-507 and the temperature peaks of the target 601-607. In the example shown in FIG. 5, the treatment area was pre-cooled by means of direct air cooling for 10 seconds, after which light pulses were applied by a laser system, having a beam size of 5.0 mm and a square profile, a wavelength of 1726 nm at 22 watts and duration of 150 milliseconds with a separation period of 2.1 seconds, while cooling remains active. In this example, the direct air cooling used for pre-cooling and during the treatment delivers a high-speed column of air, cooled to −22° C., determining a heat transmission coefficient between the skin and the air of around <H=600 W/m^2 K.

The exact size of the laser beam can be adjusted, for example using the collimating lens, according to the size of the treatment area, the power profile of the laser, the position of the treatment area of the body and other factors.

Continuing to refer to FIGS. 4, 5 and 6, the light pulses 401, 402, 403, 404, 405 and 406 essentially cause a pre-conditioning effect, as the temperature on the surface of the skin increases from around 20° C. at the peak 501 to around 44° C. at the peak 506, correspondingly the temperature of the chromophore rises from around 55° C. at the peak 601 to around 75° C. at the peak 606. In this way, simply by repeatedly applying light pulses with the same characteristics, the pre-conditioning and treatment protocols are effectively integrated, thus eliminating the need for a separate pre-conditioning system and a protocol different from the system and from the photo-treatment protocol.

It should also be noted that the number of light pulses applied for the purposes of pre-conditioning is slightly higher than the number of light pulses that perform the treatment. This characteristic is inverted in relation to existing treatment systems, which tried to reduce the amount of time employed for pre-conditioning to a minimum, due to the difficulties in balancing the effects of pre-cooling and pre-conditioning for the management of pain during treatment. The system and the methods described herein eliminate the concern of reducing the pre-conditioning time to a minimum, as the treatment uses the same settings of the pulses used for pre-conditioning.

The requisites for the success of targeted photothermal treatment of specific chromophores with minimum discomfort of the patient include:

1) ensuring that the peak temperature value in the epidermis is below around 55° C., and in any case between 45 and 60° C.

2) preventing overheating of the dermis by means of balancing of the average power of the treatment pulses with the heat removal of the cooling system; and 3) selective heating of the target chromophore, such as a peak temperature of over 55° C. for treatment of the sebaceous gland.

The embodiments described herein achieve the same effects as existing systems, with a much simpler system and protocol.

It should be noted that the number of pulses applied (N) during the treatment protocol can range from 2 pulses to around 100 pulses, according to variables such as cooling effectiveness, laser power, pulse amplitude and pulse frequency. Moreover, the number of pulses applied (N) depends on the age, race and gender of the patient.

Alternatively, a raster scanning process can be used for continuous-wave laser scanning through the treatment area, rather than applying a laser pulse to a particular block, then moving the laser to another block to apply another laser pulse. In this case with the raster scanning, the temperature increase in the sebaceous gland can be calculated as a convolution of the sizes of the sebaceous gland and of the scanning speed of the beam.

A benefit of the treatment protocol described above is that the first pulses of the sequence can function as measuring "probes" to provide important information on a specific treatment scenario.

It is known in the literature that the parameters of the tissues, such as the thickness of the epidermis and of the dermis, vary according to the individual, based on factors such as age, gender and ethnicity, and between the different areas of the skin. For example, the skin on the forehead has different properties to the skin on the back, even in the same individual, thereby making different treatment parameters necessary for different treatment positions. Consideration of these variations in the properties of the tissue in determining the specific treatment protocol is significant for the treatment of acne with the laser.

As an example, in the laser treatment of acne, the thermal operating range is generally linked to the upper surface of the epidermis and to the damage threshold temperature of the dermis of around 55° C., and to the lower temperature limit required to take the sebaceous gland to its damage threshold, which is around 75° C. As there is no method for directly measuring the temperature of the sebaceous gland that is targeted by the treatment protocol, the surface temperature of the skin can provide an indication of the temperature of the sebaceous gland, more in general of the target. A correlation model that provides the correspondence between the temperature of the sebaceous gland and more in general of a target within the skin and the temperature of the surface of the skin can thus be used to adapt the treatment protocol. The correlation model can be developed using, for example, an analytical heat transfer model, correlating the surface temperature of the skin to the damage of the sebaceous gland, more in general to the target, given the application of specific treatment protocol. In the present invention this correlation model is executed by the computer 121, which analyses, in real-time, the data from the skin temperature sensor 128 and the cooling sensor 112. It is processed by means of a finite element calculation. The physical constants included in this model (such as specific heat, skin density) are entered in a database in the memory of the computer 121. According to the portion of tissue involved in the treatment and selected by the user/dermatologist, these constants are retrieved and appropriately included in the correlation model.

In particular, considering a specific point of the skin and based on the value of the power of the electromagnetic radiation emitted by the laser system 124 and measured by the photodiodes 125, on the temperature, pressure and velocity of the flow of cooling fluid, for example air, measured by the sensors 112, and on the surface temperature of the skin measured by the sensor 128, the temperature of the target is determined by means of the following equations.

where, $$Q = H \cdot (T_{air} - T)$$
$$\rho C_p \frac{\partial T}{\partial t} + \rho C_p u \nabla T + \nabla q = Q + Q_{bio};$$
$$q = -k \nabla T$$

ρ, k, Cp are respectively: density, thermal conductivity and thermal capacity at constant pressure relating to the specific location of the treatment on the skin (forehead, back, cheek, etc.), age, gender and race of the patient set by the operator/dermatologist;

Q is the quantity of heat that is generated as a result of absorption of the laser radiation knowing the power of the laser radiation measured by the photodiodes 125 and $Q_{bio}$ is the metabolic heat of the tissue that is measured by the sensor 128 before the cooling and heating actions;

$T_{air}$ is the temperature of the cooling agent measured by the sensors 112,

T is the temperature measured by the sensor 128.

Therefore, starting from the temperature measurement of the surface of the skin 170 implemented by the sensor 128 the model processes a three-dimensional profile of the portion of tissue that is to be treated and assigns an initial temperature value to each point thereof. The effect of the cooling fluid on the surface is then evaluated, starting from the values of temperature, pressure and velocity of the cooling flow measured by the sensors 112 and from the surface temperature value of the skin measured by the sensor 128.

Starting from the measured values and knowing the parameters of the laser radiation, the model is able to supply the temperature in all portions of the tissue.

Moreover, the model is able to predict the dissipation mode of the heat absorbed in time, again on the basis on the equations described above.

Therefore, in the present invention the user/dermatologist can know the temperature of the sebaceous gland, more in general target, through the display 126 due to the correlation model executed by the computer 121 that analyses the data supplied in real-time by the skin temperature sensor 128 and by the cooling sensor 112.

For example, it is known that the damage temperature of the sebaceous gland is higher than 75° C. At a surface temperature of the skin below 40° C., 505, it has been determined that there is no damage to the sebaceous gland, in fact the temperature 605 is below 75° C. When the temperature of the surface of the skin is between 40° C. and 55° C., 506, there are different degrees of damage to the sebaceous gland, up to its destruction as the temperature at 606 and 607 is higher than 75° C. With this procedure it is possible to ensure that there is no thermal damage to the epidermal and dermal tissues.

An innovative analysis protocol can be incorporated in the treatment method to directly determine personalised treatment parameters, extrapolating from the measurements of the final temperature of the epidermis a treatment at lower laser powers, to avoid damage to the epidermis and effectively damage the sebaceous glands. In this way, the treatment protocol can be personalised for a specific treatment area for an individual and diminishes the variations of the treatment that can be caused by variations of the laser power of a specific machine, and variations in the treatment conditions, such as ambient humidity, air pressure and temperature.

For example, by directly measuring the surface temperature of the skin 501-504, during the first four pulses 401-404, the maximum surface temperature of the skin after application of the subsequent pulses 507 can be predicted with a high level of precision using the curves of the peaks of FIGS. 5 and 6. Therefore, due to the correlation method executed by the computer 121, we can predict when the damage temperature of the sebaceous gland, or more in general of the target, is reached. This prediction can be used to modify, through the controller 122, the specific parameter of the laser treatment protocol 128 and the cooling 110, to reduce the number of pulses applied, adjust the duration of the pulse or modify the power of the laser for the subsequent pulses, and reach, in all cases of skin condition (age, gender, position, race) the damage temperature of the target. This personalisation process greatly improves the comfort and the safety of the patient during the treatment procedure.

In an embodiment, the controller 122 under the analysis executed by the computer 121 could send a trigger to the controller of the scanner 205 so as to guide the scanner in the most efficient way to avoid, for example, superimposing of heat between adjacent points, modifying the range of values or sequence mode: 303, 304, 305 and 306 could become 304, 305, 303 and 306, etc.

Figure 7:
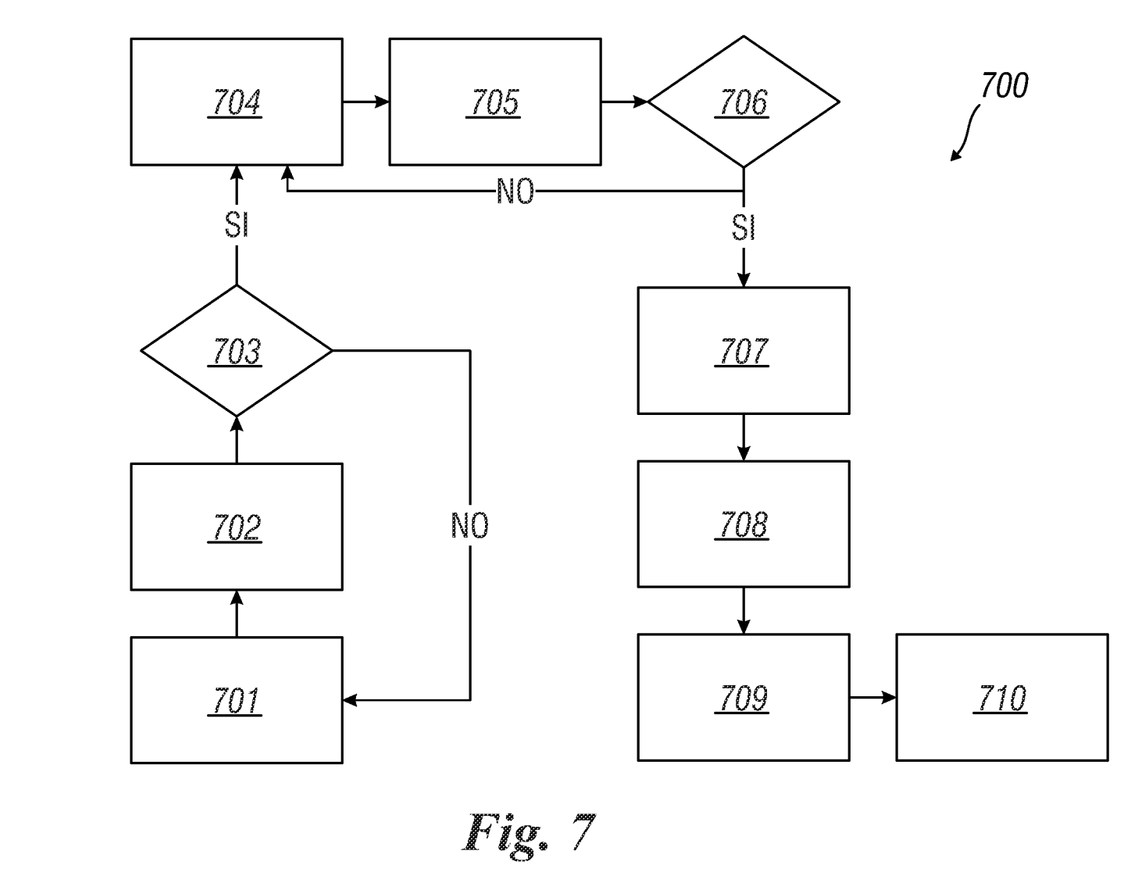
FIG. 7 shows a flow diagram that illustrates an example of a process for analysing the surface temperature of the skin measured, predicting the temperature of the skin when subsequent pulses are applied, and modifying the treatment protocol accordingly.

FIG. 7 shows a flow diagram illustrating an example of a process for the analysis protocol, executed by the computer 121 and by the controller 122, according to an embodiment. The analysis protocol functions during the pre-cooling step (701, 702 and 703) and during the laser and cooling steps (704, 705, 706, 707, 708 and 709) and post-cooling step (710). The analysis protocol assumes that the distribution of the temperature of the skin surface during pre-cooling is as uniform as possible (for example +/−2° C.). Therefore, the analysis protocol assumes that the maximum temperature of the surface of the skin and the temperature of the damage threshold for the target (for example the sebaceous gland) are known. Moreover, a correlation model between the surface temperature of the skin and the target (e.g. the sebaceous gland) has been established using computational analysis, for example finite element modelling of the heat transfer.

As shown in FIG. 7, an analysis protocol 700 starts applying pre-cooling to the treatment area in the step 701. The temperature and the pressure of the cooling fluid are monitored by the cooling sensor 112, the temperature of the skin is monitored by the heat sensor 128. The surface temperature of the skin in the treatment area is then measured in a step 702. If it is sufficiently uniform, in a possible embodiment +/−2° C., the protocol goes on to the step 704 of applying the laser to the area to be treated. Otherwise, the computer 121 and the controller 122 act on the cooling unit of the controller 111 to obtain uniformity of distribution of the desired temperature.

Therefore, an analysis protocol 700 starts applying a low power laser pulse. The power of the laser, monitored by the photodiode 125, should be set to values that are below the damage threshold for the skin. The surface temperature of the skin in the treatment area is then measured in a step 705. The temperature can be measured, for example, using an infrared camera or similar apparatus. It is then decided 706 whether enough data has been gathered to adapt the data gathered to the correlation model predetermined by the computer 121. If the answer to the decision 706 is no, then the process returns to step 704, at which point a laser pulse at a different lower power setting is applied by the controller 122 to the treatment area to gather further correlation data between the laser power applied and the temperature of the skin. If necessary, the controller 122 could change the cooling parameter through the cooling unit of the regulator 111.

If the answer to the decision 706 is yes, the analysis protocol 700 proceeds to adapt the data of the cutaneous temperature measured to the correlation model established in a step 707. Subsequently, the parameters of the laser and cooling system for the specific treatment area for the individual are determined by the computer 121 in a step 708. They are sent by the controller 122 to the laser 124 and to the cooling system 110. Finally, in a step 709, the exact treatment protocol to be used for the specific treatment area for the individual is modified according to the appropriate laser and cooling parameters found in step 708.

The analysis protocol can be performed before the actual treatment session, for example, when the patient is checked in for an appointment or in a pre-treatment session. As lower powers are used, the analysis protocol can be performed without the need for local anaesthetic, ensuring that no epidermal or dermal damage occurs during the analysis step. For example, in preparation for the treatment, a skilled operator can quickly perform a pre-measurement of the various treatment points and, with a scan of the skin, develop a personalised treatment protocol.

After establishing the relation between the laser power and the temperature of the surface of the skin for a patient and/or a position of the skin and/or a device, this relation can be used to continuously adjust treatments in progress.

It is demonstrable that the relation between power of the laser system and temperature of the surface of the skin is linear. The level of slope varies according to the type of area on which the treatment is being performed. Consequently, for a given patient and for a specific portion of skin, it is possible to perform a series of treatments at low power values so as to obtain a linear extrapolation at high power values. By low power values we mean levels of delivered power that do not cause any type of damage or pain to the patient. Naturally, the feedback system, characteristic of this invention also at low laser power, ensures that no damage is caused to the biological tissue at higher powers, due to the predictive process described above. On the basis of the temperature of the skin, reached in the previous treatment position, the dermatologist can be given advice for adjusting the power and cooling parameters of the laser, or the device can be adjusted automatically for the next treatment position.

On the basis of the above description, it is evident that the protocol described allows management of all the variations of the parameters that fall within a dermatological treatment, parameters relating to biological tissue (different types of skin, different portions of skin, etc.), to the treatment target, and to setting of the treatment system.

Our predictive method functions irrespective of the ambient temperature value, of the value of the surface temperature of the skin in conditions of equilibrium, of the physiological conditions of the skin (such as perfusion speed or blood temperature) of the effects of external pressure and, more in general, on external environmental conditions (such as wind speed).

Figure 8:
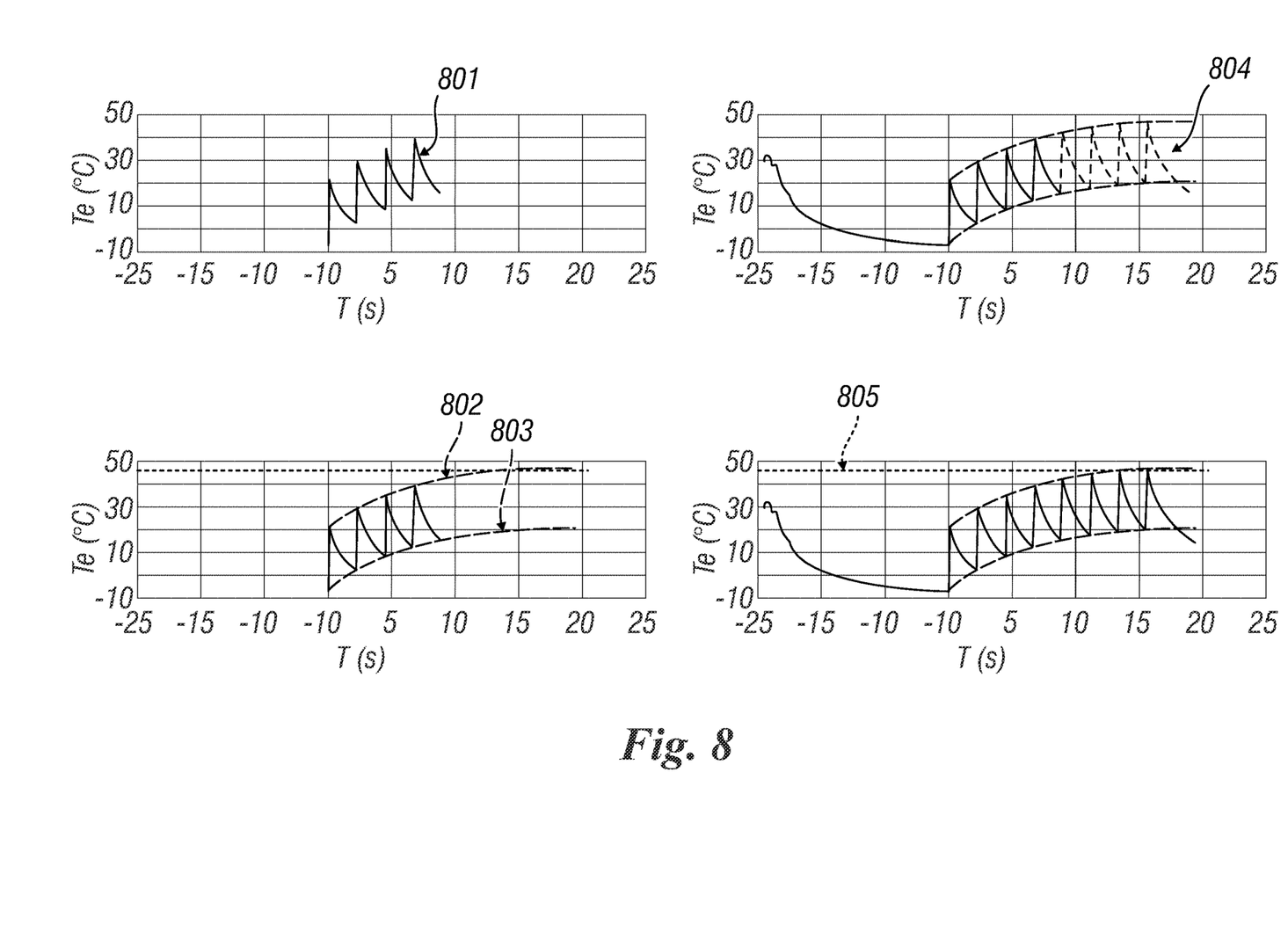
FIG. 8 shows graphs of the temperature measured to perform a prediction of the temperature and hence manage the adaptation technique.

The system, after having acquired the surface temperature profile 801 generated by the first laser pulses, for example 4, performs a prediction for the maximum temperature values 802, and preferably also for the minimum values 803 according to the equations:

$$T_{max} = T_{0max} - T_{1max} e^{\frac{-t}{T_{0max}}}$$

$$T_{min} = T_{0min} - T_{1min} e^{\frac{-t}{T_{0min}}}$$

These two curves represent the prediction lines of the peak temperature 802, 803, ($T_{0max}$ and $T_{0min}$ respectively), which correspond to the continuation of the envelope of the measurements performed.

$T_{max}$ and $T_{min}$ are the curves that represent the envelope of the temperatures measured and those predicted.

$T_{1max}$ and $T_{1min}$ represent the temperature values representative of the effect of the first pulse on the surface of the skin.

$T_{0max}$ and $T_{0min}$ represent the growth rates of the temperature on the surface of the skin as an effect of the laser pulses.

The system is now able to predict the subsequent pulses of the treatment, for example the subsequent 4 pulses 804 so that it is possible to reach the maximum surface temperature 805 that allows thermal damage to the target to be achieved avoiding damage to the surrounding tissue. Each of the parameters used in this predictive protocol is a function of the process parameters. Consequently, by varying the latter it is possible to control all the variations of the process variables. In detail, by varying the power of the laser source the thermal gradient 801 varies linearly. The examples provided above refer to damage of the sebaceous gland for the partial and/or permanent cure of acne. However, it is evident to the person skilled in the art that the device and the method of this invention is applicable to all fields of dermatology, in particular to hair removal.

The invention claimed is:

1. A system for the treatment of targets under the skin of a patient, comprising:
    a laser device for emitting a first series of laser pulses towards an area of the skin of a patient, where a target to be reached by said laser pulses is located under said skin;
    a cooling system of said area of the skin, said cooling system adapted to use a cooling fluid;
    a first measurement sensor of a first temperature of said area of skin;
    a second measurement sensor of the temperature of said cooling fluid;
    a computer which receives the signals from said first and second temperature measurement sensors;
    said computer controls said laser device that emits a first series of laser pulses having a predetermined power, duration and temporal spacing;
    said first measurement sensor measures the temperature of said area of skin, following said first series of laser pulses;
    said computer calculates a predicted temperature prospectively reached in said area of the skin following the emission of a prospective second series of pulses having said predetermined power, duration and temporal spacing;
    wherein said predicted temperature is calculated via a correlation model relating skin temperature to target temperature, said correlation model utilizing physical constants of said skin, in order to determine when a specific damage temperature of said target is reached;
    wherein the computer is adapted to calculate the predicted temperature reached of said area of the skin by means of a prediction of a measured temperature envelope of said area of skin, following said first series of laser pulses; and
    wherein the computer is adapted to vary any of said predetermined power, duration, and temporal spacing of said series of pulses, or the temperature of said cooling fluid on the basis of the value of said predicted temperature reached of said area of the skin.

2. The system according to claim 1, characterised in that said computer calculates the number of pulses necessary to reach a first predetermined temperature of said area of skin.

3. The system according to claim 2, characterised in that said first predetermined temperature ranges from 45 to 60° C.

4. The system according to claim 1, characterised in that said computer calculates a first temperature of the target placed at a predetermined depth from said area of the skin in relation to said first temperature of said area of skin.

5. The system according to claim 4, characterised in that said computer calculates a predicted target temperature prospectively reached of said target following the emission of the prospective second series of pulses.

6. The system according to claim 5, characterised in that said computer varies any of said predetermined power, duration and temporal spacing of said series of pulses, or the temperature of said cooling fluid based on the value of said predicted temperature reached of said target.

7. The system according to claim 1, wherein the physical constants comprise at least one of specific heat and skin density.

8. The system according to claim 1, wherein the predicted temperature is a maximum surface temperature reached in said area of the skin after a plurality of subsequent series of pulses having said predetermined power, duration and temporal spacing.

\* \* \* \* \*